(12) United States Patent
Choudhary et al.

(10) Patent No.: US 10,562,829 B1
(45) Date of Patent: Feb. 18, 2020

(54) HIGHLY SELECTIVE OLEFIN REMOVAL WITH UNSULFIDED HYDROTREATING CATALYSTS

(71) Applicant: PHILLIPS 66 COMPANY, Houston, TX (US)

(72) Inventors: Tushar Choudhary, Bartlesville, OK (US); Tu N. Pham, Bartlesville, OK (US); Sundararajan Uppili, Jersey Village, TX (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 16/212,186

(22) Filed: Dec. 6, 2018

(51) Int. Cl.
| | | |
|---|---|---|
| *C07C 5/11* | (2006.01) | |
| *C07C 5/03* | (2006.01) | |
| *C07C 7/12* | (2006.01) | |
| *C10G 45/28* | (2006.01) | |
| *C10G 45/08* | (2006.01) | |
| *C10G 45/02* | (2006.01) | |
| *C10G 45/30* | (2006.01) | |
| *C10G 45/06* | (2006.01) | |
| *C10G 45/04* | (2006.01) | |
| *C10G 45/32* | (2006.01) | |
| *C10G 45/38* | (2006.01) | |
| *C10G 45/36* | (2006.01) | |
| *C10G 45/34* | (2006.01) | |
| *C10G 45/00* | (2006.01) | |
| *C10G 45/50* | (2006.01) | |
| *C10G 45/44* | (2006.01) | |
| *C10G 45/48* | (2006.01) | |
| *C10G 45/46* | (2006.01) | |
| *C10G 69/04* | (2006.01) | |
| *C10G 69/00* | (2006.01) | |
| *C10G 69/06* | (2006.01) | |
| *C10G 69/08* | (2006.01) | |
| *C10G 69/02* | (2006.01) | |

(52) U.S. Cl.
CPC .................. *C07C 5/11* (2013.01); *C07C 5/03* (2013.01); *C07C 7/12* (2013.01); *C10G 45/02* (2013.01); *C10G 45/04* (2013.01); *C10G 45/06* (2013.01); *C10G 45/08* (2013.01); *C10G 45/28* (2013.01); *C10G 45/30* (2013.01); *C10G 45/32* (2013.01); *C10G 45/34* (2013.01); *C10G 45/36* (2013.01); *C10G 45/38* (2013.01); *C07C 2523/75* (2013.01); *C07C 2523/84* (2013.01); *C10G 45/00* (2013.01); *C10G 45/44* (2013.01); *C10G 45/46* (2013.01); *C10G 45/48* (2013.01); *C10G 45/50* (2013.01); *C10G 69/00* (2013.01); *C10G 69/02* (2013.01); *C10G 69/04* (2013.01); *C10G 69/06* (2013.01); *C10G 69/08* (2013.01)

(58) Field of Classification Search
None
See application file for complete search history.

(56) References Cited

U.S. PATENT DOCUMENTS

2002/0002315 A1\* 1/2002 Kelly ..................... C07C 7/163
585/259

\* cited by examiner

*Primary Examiner* — Ali Z Fadhel
(74) *Attorney, Agent, or Firm* — Phillips 66 Company

(57) ABSTRACT

A process is disclosed for polishing a relatively highly pure stream of aromatic material bound for use as a petrochemical feedstock wherein the stream includes olefins and especially concerning, diolefins. The process comprises hydrotreating the highly pure aromatic stream with an unsulfided cobalt molybdenum catalyst that has low saturating activity for the aromatic but is active for saturating olefins and diolefins.

6 Claims, No Drawings

HIGHLY SELECTIVE OLEFIN REMOVAL WITH UNSULFIDED HYDROTREATING CATALYSTS

CROSS-REFERENCE TO RELATED APPLICATIONS

None.

STATEMENT REGARDING FEDERALLY SPONSORED RESEARCH OR DEVELOPMENT

None.

FIELD OF THE INVENTION

This invention relates to creating high purity benzene stream and particularly for selectively removing sulfur, olefins and diolefins from benzene stream within a refinery.

BACKGROUND OF THE INVENTION

Aromatic streams, especially benzene, are highly desirable and valuable chemical feedstocks for use in making plastics. Benzene can be produced by various processes. A major source of benzene is through the recovery of aromatics created in the catalytic reforming of naphtha in a petroleum refinery. Benzene can also be made through the thermal dealkylation of toluene. A high value benzene product has strict specifications of a bromine index that must be less than 20 mg/100 g, a maximum sulfur content of less than 0.2 ppm and a non-aromatics content of less than 500 ppm. During the production in refineries, benzene tends to be contaminated with olefins and diolefins which causes the benzene to miss the required specifications. Diolefins are highly unstable and reactive, causing gum formation and other stability issues. In addition, many crude oil supplies contain sulfur and the products from refining tend to contain some small amounts even with significant sulfur removal technology in the refinery. With such a low limit, meeting sulfur specifications will often be a concern and processes for producing benzene for petrochemical use must be capable of removing excess sulfur.

Current technology suggests converting the diolefins to alkanes by selective hydrogenation at temperatures between 430° F. and 500° F. using sulfided cobalt-molybdenum or nickel-molybdenum catalysts. These sulfided catalysts capture the sulfur and cause it to adhere to the catalyst separating it from the aromatic stream. Unfortunately, in this reaction, some benzene molecules are partially hydrogenated to cyclohexene and other cycloolefins which essentially reduce the benzene yields and fails to reduce the bromine index below the specifications. All of these contaminants are typically at low concentrations, but they are still problematic and substantially compromise the value of the aromatic stream.

Another technology for dealing with diolefins and sulfur includes clay treaters which are adsorbents that reduce both the sulfur content and the diolefin content without losing benzene from the product. This clay treatment process is expensive as the disposal of contaminated clay as hazardous waste must be included in operating cost and the capital cost of a clay treater is substantial for the contribution to the minimal contaminant that must be removed.

A simple and inexpensive process of removing sulfur and diolefin content from aromatics that does not create side reactions that waste aromatics and create other problem components would provide significant advantage to the financial performance of many refineries.

BRIEF SUMMARY OF THE DISCLOSURE

The invention more particularly relates to a process for producing a high purity aromatic product such as benzene, toluene, xylene where concerns arise for olefin and diolefin content, where the process includes forming an aromatic stream comprising at least 99% by weight the aromatic product desired where the stream includes measurable diolefin content. The stream is delivered to a hydrotreater having a catalyst comprising cobalt and molybdenum and has not been treated with a sulfiding agent prior to this step of delivering the stream to the hydrotreater, wherein the temperature of the stream is between 400° F. and 600° F. In the hydrotreater at least 90 percent of the diolefins are converted to alkanes while, at the same time, less than 10 ppm of the aromatic is converted to cyclohexene such that the bromine index of the aromatic stream is reduced.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

It is conventional to gather aromatics from catalytic reforming of naphtha and separate the same for sale as a petrochemical feedstock. Hydrotreating is one process for cleaning up undesirable components in such aromatic petrochemical feedstock. The hydrotreating process is used to reduce the olefin content and especially the diolefin content. Since it is expected to have sulfur in the aromatic and removal of sulfur is needed to meet the required specifications, sulfided catalysts are used for such hydrotreating. Unfortunately, conventional hydrotreating processes tend to saturate aromatics making them in to less valuable cycloalkenes and naphthenes. After much testing and investigation, the inventors have discovered that cobalt molybdenum catalysts are far more selective for converting the olefins, diolefins and sulfur compounds to more easily handled products with very little saturating function of the target aromatic products if they are not subjected to a sulfiding treatment prior to startup in hydrotreatment. With sulfur in the feedstream, it is conventional to perform a sulfiding treatment to activate the catalyst and help it resist sulfur poisoning. With this insight, refineries are able to capture a significant financial impact to maximize on the production off-spec target material that has premium value in the market place compared to other fuel options.

This was highly unexpected as all hydrotreating catalysts that are used commercially for removing sulfur and for hydrotreating sulfided prior to use. With sulfur in the feedstream, unsulfided catalysts are expected to be poisoned by the sulfur. Anticipating sulfur to be in the feedstream, it is conventional to prepare the catalyst for operation by selecting a catalyst that will be sulfided prior to operation and performing the sulfiding treatment to it prior to hydrotreating the hydrocarbon stream. But, in accordance with the present invention, hydrotreating a high purity aromatic stream is better accomplished by selecting a catalyst that is not expected to be sulfided prior to use and not sulfiding the same prior to use. This is especially true if, to the extent that the aromatic stream contains sulfur, that such sulfur compounds are light and easy-to-treat sulfur contaminants.

While sulfided catalysts are known to be better at performing hydrodesulfurization than non-sulfided catalysts, the sulfur species in these types of aromatic streams are sufficiently easy to treat in the low concentrations that they exist, unsulfided catalyst are able to treat the aromatic stream to meet the needed specifications. The value to a refinery with a petrochemical facility readily desiring on spec purity benzene or other aromatics is quite valuable yielding multiple millions of dollars per year. This inability to meet the benzene specifications, especially the bromine index, require the installation of other systems to obtain specification. For example, a clay adsorption unit, which has a capital cost of more than $3,000,000 and substantial running costs for frequent replacement of the clay will substantially reduce or eliminate any profit potential for benzene as a petrochemical feedstock.

Test data show that using sulfided cobalt-molybdenum catalyst in a hydrotreater on a benzene or toluene sample to remove diolefin and olefin content also converts the aromatics to cycloalkenes as evidenced by a higher bromine index. Using unsulfided catalyst on the same sample turns out to reduce the Bromine Index. It is seen that the diolefins are reduced and cyclohexene content is not created or increased as shown in Tables 1 and 2 below. Table 1. Performance of a non-sulfided commercial Cobalt-Molybdenum catalyst. Data obtained with model toluene feed spiked with cyclohexadiene. Experiments were conducted at 430° F., 225 psig, 1640 scf/bbl and 4.0 hr −1 LHSV

TABLE 1

|  | Feed | Hydrotreated product | | |
|---|---|---|---|---|
| Sulfiding |  | No | No | 450 ° F. |
| Time on stream, hr |  | 48 | 77 | — |
| Aromatics [wt%] | 99.940 | 99.912 | 99.918 | 99.826 |
| Benzene | 0.016 | 0.017 | 0.017 | — |
| Toluene | 99.900 | 99.870 | 99.874 | 99.780 |
| Olefins [wt%] |  |  |  |  |
| Diolefin | 0.009 | — | — | — |
| Methyl cyclohexene | — | 0.003 | 0.002 | 0.030 |
| Naphthenes [wt%] |  | 0.044 | 0.049 | 0.063 |
| Cyclohexane | 0.008 | 0.006 | 0.006 | — |
| Methyl cyclohexane | — | 0.003 | 0.002 | 0.063 |
| Other naphthenes | — | 0.035 | 0.041 | — |
| Bromine index [mg/g] | 22 | 17 | 17 | 51 |

Table 2. Performance of a non-sulfided commercial CoMo catalyst. Data obtained with model toluene feed spiked with thiophene and cyclohexadiene. Experiments were conducted at 430° F., 225 psig, 1640 scf/bbl and 4.0 hr −1 LHSV

TABLE 2

|  | Feed | Hydrotreated product | | | |
|---|---|---|---|---|---|
| Time on stream, hr |  | 384 | 408 | 432 | 480 |
| Sulfur [ppm] | 10 | 1.0 | 3.9 | 0.9 | 0.9 |
| Aromatics [wt%] | 99.930 | 99.919 | 99.917 | 99.894 | 99.902 |
| Benzene | 0.017 | 0.018 | 0.017 | 0.017 | 0.017 |
| Toluene | 99.892 | 99.878 | 99.878 | 99.855 | 99.861 |
| Olefins [wt%] | 0.021 | 0.003 | 0.003 | 0.005 | 0.003 |
| Diolefin | 0.018 | — | — | — | — |
| Methyl cyclohexene | — | 0.003 | 0.003 | 0.005 | 0.003 |
| Naphthenes [wt%] | 0.016 | 0.046 | 0.044 | 0.051 | 0.056 |
| Cyclohexane |  | 0.015 | 0.016 | 0.015 | 0.016 |
| Methyl cyclohexane |  | 0.012 | 0.012 | 0.011 | 0.011 |
| Other naphthenes | 0.016 | 0.019 | 0.016 | 0.025 | 0.029 |
| Bromine index [mg/g] | 27 | 12 | 11 | 7 | 8 |

For comparison, a review Tables 3 and 4 show much poorer results using sulfided CoMo catalyst A and B, respectively. With these catalysts. In particular, the Bromine Index has increased well above specification and aromatic content has reduced.

TABLE 3

| Catalyst A | Feed | Hydrotreated product | | | |
|---|---|---|---|---|---|
| Hydrotreating Temperature [° F.] |  | 430° F. | 450° F. | 470° F. | 500° F. |
| Aromatics [wt%] | 99.981 | 99.670 | 99.602 | 99.513 | 99.334 |
| Benzene | 47.374 | 46.672 | 46.535 | 46.482 | 46.490 |
| Toluene | 52.340 | 52.745 | 52.815 | 52.784 | 52.598 |
| Olefins | 0.003 | 0.025 | 0.028 | 0.027 | 0.029 |
| Diolefins | 0.001 | — | — | — | — |
| Cyclohexene | 0.002 | 0.005 | 0.007 | 0.006 | 0.007 |
| Methyl cyclohexene | — | 0.020 | 0.021 | 0.021 | 0.022 |
| Naphthenes [wt%] | 0.007 | 0.251 | 0.329 | 0.434 | 0.601 |
| Cyclohexane | 0.004 | 0.087 | 0.115 | 0.154 | 0.208 |
| Methyl cyclohexane | 0.000 | 0.141 | 0.194 | 0.264 | 0.373 |
| Non-aromatics (GCLX) |  | 0.344 | 0.384 | 0.479 | 0.650 |
| Bromine index [mg/g] | 31 | 45 | 46 | 47 | 49 |

TABLE 4

| Catalyst B | Feed | Hydrotreated product | | | |
|---|---|---|---|---|---|
| Hydrotreating Temperature [° F.] |  | 430° F. | 450° F. | 470° F. | 500° F. |
| Aromatics [wt%] | 99.981 | 99.759 | 99.714 | 99.661 | 99.490 |
| Benzene | 47.374 | 46.663 | 46.498 | 46.475 | 46.529 |
| Toluene | 52.340 | 52.843 | 52.964 | 52.936 | 52.714 |
| Olefins | 0.003 | 0.020 | 0.020 | 0.018 | 0.024 |
| Diolefins | 0.001 | — | — | — | — |
| Cyclohexene | 0.002 | 0.005 | 0.004 | 0.004 | 0.005 |
| Methyl cyclohexene | — | 0.015 | 0.016 | 0.013 | 0.019 |
| Naphthenes [wt%] | 0.007 | 0.174 | 0.237 | 0.293 | 0.453 |
| Cyclohexane | 0.004 | 0.058 | 0.080 | 0.101 | 0.151 |
| Methyl cyclohexane | 0.000 | 0.095 | 0.139 | 0.176 | 0.279 |
| Non-aromatics (GCLX) |  | 0.233 | 0.279 | 0.358 | 0.496 |
| Bromine index [mg/g] | 31 | 34 | 35 | 36 | 38 |

This simple change to hydrotreating aromatics for petrochemical use will avoid spending additional capital on equipment to further clean up the target stream while bringing a profitable product to market. And the change is rather simple and straightforward for producing highly pure benzene, toluene and xylene for petrochemical use. It should be understood that this process be used in conjunction with other known processes including the clay sorbent treatment downstream of hydrotreating.

In closing, it should be noted that the discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process for producing a high purity aromatic product such as benzene, toluene, xylene where concerns arise for olefin and diolefin content, where the process comprises:

forming an aromatic stream comprising at least 99% by weight the aromatic product desired where the stream includes measurable diolefin content;

delivering the stream to a hydrotreater having a catalyst comprising cobalt and molybdenum and has not been treated with a sulfiding agent prior to this step of delivering the stream to the hydrotreater, wherein the temperature of the stream is between 400° F. and 600° F.; and converting at least 90 percent of the diolefins to alkanes in the hydrotreater while, at the same time, converting less than 10 ppm aromatic to cyclohexene such that the bromine index of the aromatic stream is reduced.

2. The process according to claim 1 wherein any sulfur in the aromatic stream is converted to hydrogen sulfide in the hydrotreater and removed from the aromatic stream downstream of the hydrotreater.

3. The process according to claim 1 wherein the pressure in the hydrotreater is between 175 psig and 275 psig.

4. The process according to claim 1 wherein the liquid hourly space velocity in the hydrotreater is between 2 and 8 $hr^{-1}$.

5. The process according to claim 1 wherein the aromatic stream includes sulfur species and where the process further includes adhering sulfur species to a sorbent to further reduce the sulfur content of the aromatic stream.

6. The process according to claim 1 wherein the measurable diolefin content is 0.001 wt % or more.

* * * * *